(12) United States Patent
Tenne et al.

(10) Patent No.: US 7,449,340 B2
(45) Date of Patent: Nov. 11, 2008

(54) METHOD FOR THE EARLY DIAGNOSIS OF CANCER

(75) Inventors: Gil Tenne, Shoham (IL); Mark L. Levitt, Hashmonaim (IL); Anahit Karapetian, Tel Aviv (IL)

(73) Assignee: Era-Massis, Inc., Wilmington, DE (US)

( * ) Notice: Subject to any disclaimer, the term of this patent is extended or adjusted under 35 U.S.C. 154(b) by 782 days.

(21) Appl. No.: 09/927,084

(22) Filed: Aug. 9, 2001

(65) Prior Publication Data

US 2003/0044881 A1 Mar. 6, 2003

(51) Int. Cl.
*G01N 1/00* (2006.01)
*G01N 1/18* (2006.01)
*G01N 33/554* (2006.01)
*G01N 33/569* (2006.01)
*G01N 33/574* (2006.01)

(52) U.S. Cl. .................. 436/174; 435/7.2; 435/7.23; 435/7.32; 435/7.33; 435/7.34; 435/7.35; 435/7.95; 435/340; 435/344; 435/372.1; 436/17; 436/64; 436/177

(58) Field of Classification Search .............. None
See application file for complete search history.

(56) References Cited

U.S. PATENT DOCUMENTS

| | | | |
|---|---|---|---|
| 3,476,514 A | 11/1969 | Roth | 23/230 |
| 5,344,762 A * | 9/1994 | Karapetian | 435/39 |
| 5,455,160 A | 10/1995 | Fagerhol et al. | 435/7.23 |
| 5,952,200 A | 9/1999 | Johnson et al. | 435/91.2 |

FOREIGN PATENT DOCUMENTS

| | | |
|---|---|---|
| EP | 0685739 | 8/2001 |
| GB | 1587244 | 4/1981 |

OTHER PUBLICATIONS

English Abstract of JP56166124A2 dated Dec. 21, 1981.
English Abstract of JP6258324 Dated Sep. 16, 1994.
Report of a WHO Expert Committee "Early Detection of Cancer" *World Health Organization Technical Report Series*, No. 422, (1969).
Oleinik, S.F., et al. "Carcinolytic and Carcinogenic Intestinal Coliflora" *Vrachebnoye-delo*, vol. 5, p. 13-17, (1968).

* cited by examiner

*Primary Examiner*—Mark Navarro
*Assistant Examiner*—J. Hines

(57) ABSTRACT

The present invention relates to a method for the early diagnosis of cancer in a subject, which is based on determination of the relative fraction of microorganisms derived from the feces of the subject, as compared to the total count of microorganisms in the same of corresponding sample. This relation has been found to be indicative of the presence or absence of cancer in said subject.

After isolating at least one of the microorganisms from the fecal sample to form a so-called diagnostic sample, and incubating, for a sufficient time, the diagnostic sample with cancer cells. The microorganism being in an amount corresponding to its relative fraction in the original fecal sample, the cancerolytic activity of the microorganism/s is indicative to the presence or absence of cancer cells in the subject. The cancerolytic activity is expressed by terms of a tumor cell necrosis index (TCNI).

Further, the method of the invention is based on determining level of expression or level of activity of L-PAR II in a fecal-derived microorganism/s sample, the level determined being also indicative of the presence or absence of cancer cells in the subject from which the fecal sample was derived.

19 Claims, 2 Drawing Sheets

METHOD FOR THE EARLY DIAGNOSIS OF CANCER

FIELD OF THE INVENTION

This invention relates to methods for the early diagnosis cancer.

BACKGROUND OF THE INVENTION

It is generally agreed at early diagnosis of cancer is almost always a prerequisite of successful treatment. For example, the WHO Expert Committee's Report on Early Detection of Cancer (1969) stated that over half of cancer patients could have been cured if the disease had been detected at an early stage and treated soon after detection. In view of the widespread incidence of the disease, mass screening techniques would evidently be of great value, such as is available, for example, at least in developed countries, in the field of tuberculosis of the chest by means of mass X-ray examination.

Among previous proposals for the diagnosis of cancer may be mentioned the following. In U.S. Pat. No. 3,476,514 there was described a method of detecting cancer cells by staining test cells with acriflavine-HCl solution, determining indirectly the dye absorbed by the test cells and comparing with a control JP 56166124A2 proposed a method for diagnosing malignant tumors which utilized an injectable composition containing an endotoxin extracted from cultured bacteria. In GB 1587244, there was described inter alia, the use in a serum agglutination test on the sera of patients, for the detection of neoplasm, of an antigen produced by a species of the genus *Streptococcus*.

Bodily health is known to be affected by the nature of the intestinal flora which apparently influences, for example, metabolic processes and both local and general body immune response. It has also been known for some time that certain of the intestinal flora bacteria of normal humans have oncolytic activity, and that there exists a relationship between intestinal microfloral composition and cancer morbidity, see e.g., Oleynik, S. F. and Panchishina, M. V., "About Coliflora and Cancerolycity and Carcinogenicity of the intestine", Vrachebnoye-delo, 5:13-17 (1968).

There are several publications relating to the use of fecal samples for the detection of cancer. For example, EP 685739 described a method for the diagnosis of colorectal cancer comprising reaction anti-DAF antibodies with a supernatant of a fecal sample thereby forming an antigen-antibody complex and measuring the amount of complex formed. Another publication is U.S. Pat No. 5,952,200 which describes a test for diagnosing the presence of cancerous cells in samples of human tissue, fluids or semi-fluids such as feces, by the detection of transcripts for stromelysin0-3 in the tissue cells.

JP 6258324 describes a method for the diagnosis of digestive-system cancer disease by using an antibody selective to variation-type protein of the cancer-suppressing gene P53, while U.S. Pat. No. 5,455,160 describes a method for determination of fecal calprotectin as a parameter for monitoring Inflammatory Bowel Disease and gastrointestinal cancer.

Finally, U.S. Pat. No. 5,344,762 describes a method for early diagnosis of cancer by incubating in vitro a human fecal sample including bacteria with a standard culture of a known number of cancer cells. After a time period the number of cancer cells interacted and non-interacted with the bacteria is counted and the results are used for determination of a disease state.

SUMMARY OF THE INVENTION

It has now been found that healthy individuals and cancer patients show striking differences in their fecal microflora. In particular, healthy individuals were shown to present a higher percentage of *Esherichia coli* (*E. coli*) with cancerolytic activity as compared to the microflora of cancer patients.

Thus, according to a first of its aspects, the present invention provides a method for the early diagnosis of cancer in a subject, the method comprising the steps of:
  i) providing a fecal sample from said subject;
  ii) treating said sample to obtain a feces-derived microorganisms sample;
  iii) identifying in the microorganism sample one or more types of microorganisms contained therein and;
  iv) determining for said one or more microorganisms its relative fraction from the total count of microorganism in said sample or in a corresponding sample, the relative fractions being indicative of the presence or absence of cancer is said subject.

The term "early diagnosis of cancer" as used herein interchangeably with the terms "early detection of cancer", "cancer screening" or "confirmation of cancer" is intended to convey such diagnosis, whether or not the cancer has reached the stage in which it is detectable by other methods presently available to the clinician.

The present invention also provides, according to a second of its aspects, a method for an early diagnosis of cancer in a subject comprising the steps:
  i) providing a fecal sample from said subject;
  ii) treating said fecal sample to obtain a feces-derived microorganism sample therefrom;
  iii) identifying in the bacteria sample one or more types of microorganisms;
  iv) determining for each of said microorganisms its relative fraction from the total count of microorganisms in said sample or in a corresponding sample;
  v) isolating one or more microorganisms from said sample for which their relative fraction was determined;
  vi) preparing a diagnostic sample containing one or more of the isolated microorganisms, the fraction of the microorganisms in said diagnostic sample corresponding to the relative fraction thereof in the fecal sample, as determined in step (iv); and
  vii) interacting said diagnostic sample with cancer cells for a time period sufficient to detect lysis of said cancer cells by the microorganism in said diagnostic sample, thereby determining for said fecal sample a tumor cell necrosis index (TCNI).

As indicated above, the diagnostic sample may contain one or more microorganisms. When containing a single microorganism, the latter is diluted in the suitable medium to a concentration corresponding to its relative concentration in the original fecal sample. However, when using two or more isolated microorganisms they are re-mixed to form a dispersion of microorganisms in which the fraction of each microorganism corresponds to its relative fraction in the original fecal sample. The formation of the diagnostic sample may be referred to herein, at times, as the re-mixing step.

An important feature of this aspect of the invention involves removal of contaminations from the sample before preparing the diagnostic sample from the isolated microorganism according to their relative fraction in the original fecal sample. Therefore, treating the fecal sample to obtain a feces-derived microorganism sample therefrom includes, removal of undesired contamination from the fecal sample to obtain an uncontaminated feces-derived microorganism sample. It has been found that the presence of contamination form the feces-derived microorganism samples, results in deviation in the value obtained for the TNCI.

Finally and in accordance with a third aspect of the present invention, there is provided a method for an early diagnosis of cancer in a subject comprising the steps:

i) providing a fecal sample from said subject;
ii) treating said sample to obtain a feces-derived microorganism sample;
iii) identifying in the microorganism sample one or more types of microorganisms contained the and isolating at least one microorganism capable of expressing in a healthy subject L-asparaginase II (L-PAR II); and
iv) determining level of expression of L-PAR II by the isolated microorganism or level of asparginase hydrolysis by said L-PAR II, said level is indicative of the presence or absence of cancer cells in said subject.

As will he shown in the following non-limiting examples, the level of expression L-PAR II or level of asparginase hydrolysis by the enzyme indicates the probability of an individual to have cancer. In particular, low levels of expression of L-PAR II as well as low levels of asparaginase hydrolysis may suggest the high probability of a subject to have cancer.

DETAILED DESCRIPTION OF THE INVENTION

The present invention is based on the finding that there is a correlation between the relative fraction of microorganisms in the feces and the probability of a subject to have cancer. In addition, when incubating standard cancer cells with specific microorganisms isolated from feces of a subject susceptible of carrying cancer cells, the microorganisms being mixed in a relation corresponding to that present in the feces of the individual, their capability to lyse the cancer cells was found to be indicative of the absence or presence of cancer cells in the subject and of tie level of disease in said subject.

Figure 1:
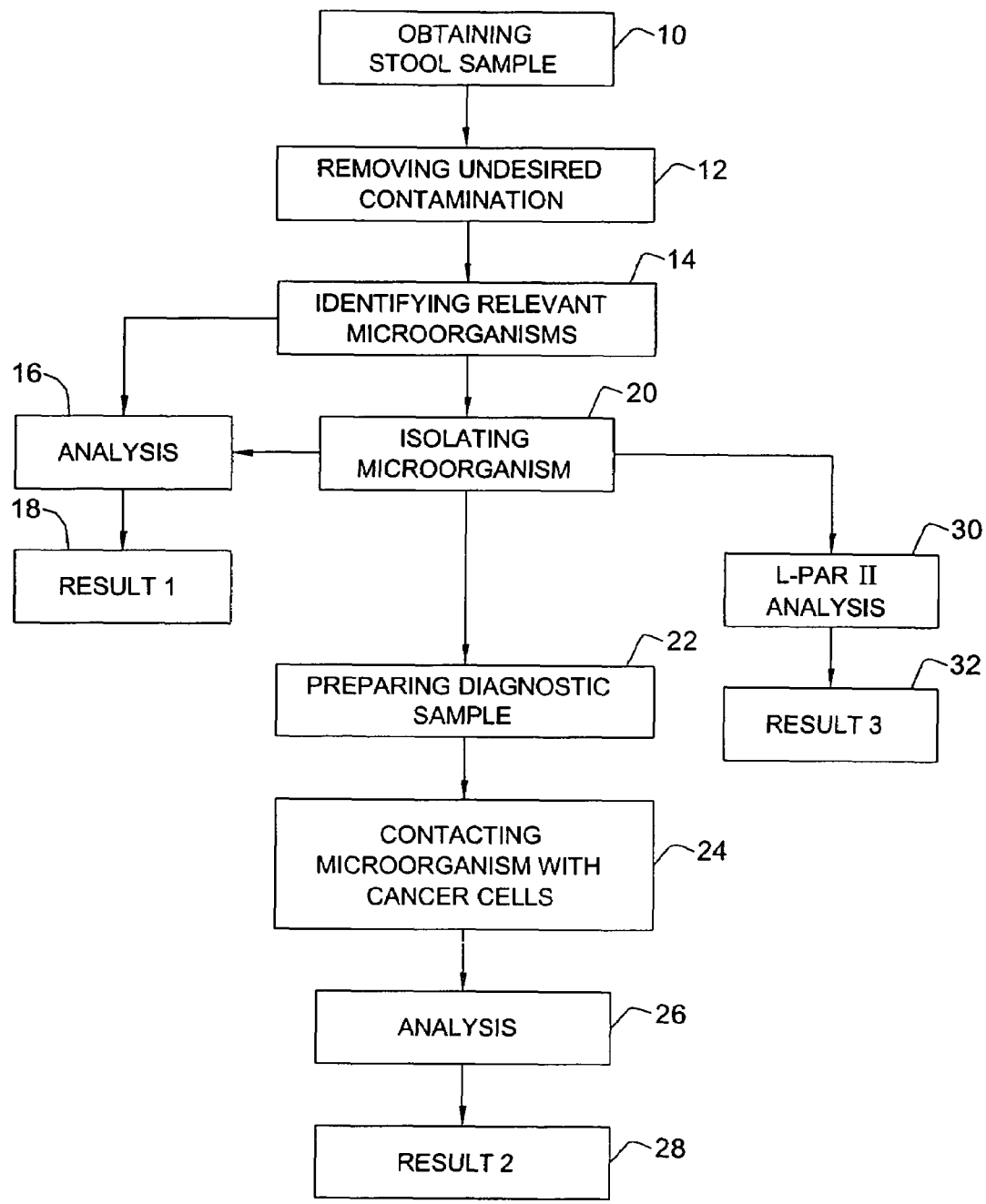
FIG. 1 is a schematic illustration of the method of the present invention.

FIG. 1 provides a schematic illustration of the different aspects of the method of the present invention.

Thus, according to a first of its aspects, the present invention provides a method for the early diagnosis of cancer in a subject. The method comprises the steps of (i) providing a fecal sample (step 10) from said subject; (ii) treating said sample to obtain a feces-derived microorganisms sample, for example, by removal therefrom undesired contamination (step 12), such as aggressive microorganisms which may lead to deviation in the screening; (iii) identifying in the microorganism sample one or more microorganisms contained therein (step 14); and (iv) finally determining for each of said microorganisms its relative fraction from the total count of microorganisms in said sample or in a corresponding sample (i.e. a second sample from the same subject, being treated in the same manner as the tested sample) (step 16), the relative fractions being indicative of the prescence or absence of cancer in said subject (step 18).

The subject to be diagnosed for cancer is preferably a mammalian animal and more preferably a human.

According to one embodiment, any type of the various types of malignant neoplasms derived from epithelial tissue (i.e. carcinomas) may be detected by the method of the present invention. As will be appreciated by those versed in the art of medicine, such neoplasms occur frequently in the skin, large intestine, lung, prostate gland and breasts among other organs. Therefore, according to one preferred embodiment the method of the present invention may be utilized for the early detection of any one of the above carcinoma.

The relative fraction in the fecal sample of each type of the microorganisms is determined by calculating the percentage of said microorganism from the total count of microorganisms in the same feces derived sample. In order to determine the same, microorganisms are preferably first treated, e.g., to remove undesired contaminations, followed by isolation of the microorganisms by any conventional isolating technique. For example, the microorganisms may be isolated by colonies formation on selective culture mediums, as will be further detailed hereinafter.

According to one embodiment the microorganisms employed by the screening method of the present invention are bacteria. One group of feces-derived bacteria includes, without being limited thereto, gram-negative anaerobic bacteria. Examples of such gram negative bacteria that typically inhabit the intestinal tracts *Escherichia, Salmonella, Shigella, Kelbsiella, Yersinia Enterobacter, Hemophilus, Gardnerella* and *Pasteurella*.

According to one preferred embodiment, the bacteria employed by the method of the present invention are *E. coli*. These bacteria may be isolated from the feces-derived sample by the use, for example, of culture medium selective for *E. coli*, such as MacConkey agar or m-Endo agar.

In addition, the bacteria may be a gram-positive bacteria. Examples of gram-positive bacteria include, inter alia, *Staphylococcus, Enterococcus, Streptococcus, Luctococcus*. According to one preferred embodiment the bacteria is *Streptococcus bovis* or *Enterococcus sp*.

The *Enterococci* coliform may be isolated from the fecal sample by culturing the feces-derived sample on a culture medium selective for *Enterococcus*. Non-limiting examples of *Enterococcus* selective mediums include Slanetz-Bartley agar and Bile-esculine-azide agar.

Evidently and as will be further explained in the following description, the screening method of the present invention involve determination of the relative fraction of a single type of bacteria or of several bacteria in order to determine the probability of a subject to have cancer. Each kind of bacteria being identified and isolated as described above.

Referring again to FIG. 1, the screening method of the present invention may include the additional steps of (v) isolating one or more microorganisms from the sample for which their relative fraction was determined (step 20); (vi) preparing a diagnostic sample containing one or more of the isolated microorganisms, the fraction of the microorganisms in the diagnostic sample corresponding to the relative fraction thereof in the fecal sample, as determined in step (iv) (step 22) Dilution or re mixing of the microorganisms in a controlled manner as defined above is essential in order to increase the effectiveness of the method of the invention; and (vii) interacting (contacting) the mixture with cancer cells for a time period sufficient to detect lysis of the cancer cells by the bacterial mixture (step 24), from which a tumor cell necrosis index (TCNI) is determined for the specific tested fecal sample (steps 26, 28).

The cancer cells employed may be any standard culture of cancer cells, for example ATCC HTB-22 (MCF7). The interaction of the bacteria mixture with the cancer cells includes incubation of the bacteria and cancer cells under conditions suitable for the bacteria to act on the cells. These conditions include suitable temperature (e.g. 37° C.), and a time period (in the following examples, 4 hours), sufficient to determine the extent of interaction between the bacteria and the cancer cells, the extent of interaction is determined by the degree of lysis of the cancer cells by the bacteria mixture (the diagnostic sample). This may be observed, for example, by the aid of a microscope or an Automated Computer Assisted Microscope, wherein the number of remaining cancer cells is counted.

Figure 2A:
FIG. 2A-2B are pictures obtained by microscope of cancer cells treated with the diagnostic sample of the present invention, the diagnostic samples derived either from a healthy object (FIG. 2B) or from a cancer patient (FIG. 2A).
Figure 2B:
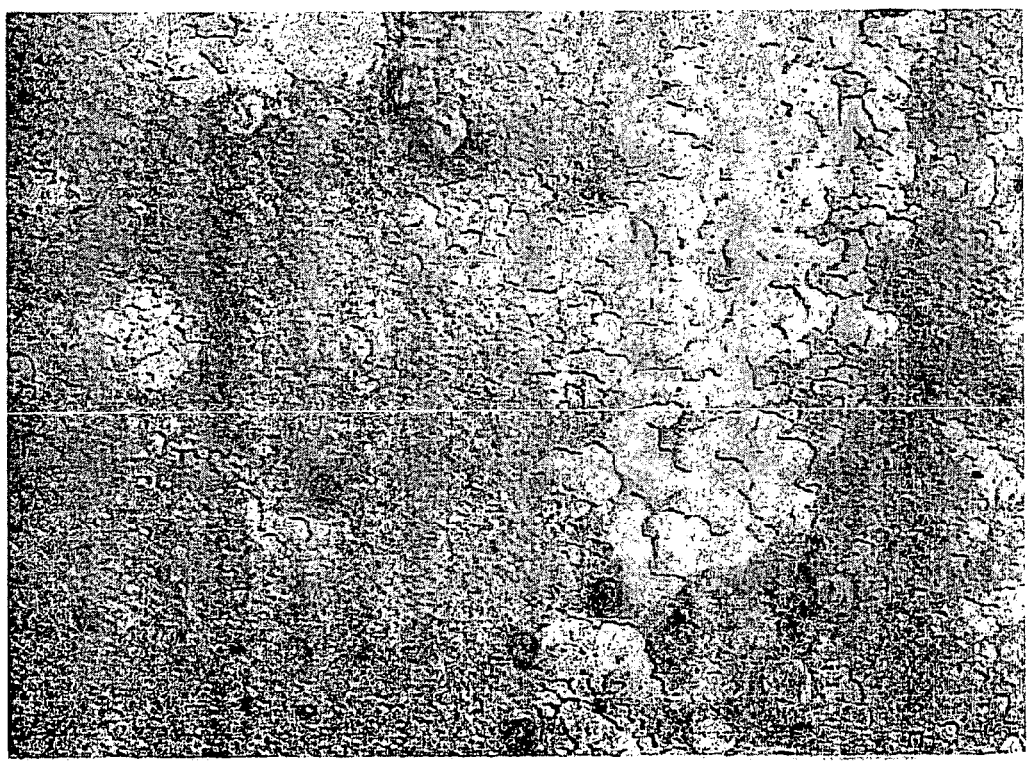

FIGS. 2A and 2B show microscope pictures obtained after incubation of cancer cells with a bacterial sample obtained from a healthy subject, (FIG. 2B) or from a cancer patient (FIG. 2A) These pictures show that in the presence of a bacterial sample obtained from a healthy subject, only a few cancer cells remain, i.e. there is an effective lysis of the cancer cells by the bacteria.

Referring again to FIG 1, the method of the invention may comprise the steps of:
 i) providing a fecal sample from said subject (step 10);
 ii) treating said sample to obtain a feces-derived microorganism sample (step 12);
 iii) identifying in the bacteria sample at least one type of microorganism capable of expressing in a healthy subject L-asparaginase II (L-PAR II) (step 14); and
 iv) determining level of expression of L-PAR II or level of activity of L-PAR II (Step 30), the level is indicative of the presence or absence of cancer cells in said subject (step 32).

L-asparaginase is an enzyme which catalyses the hydrolysis of L-asparagine to aspartate and ammonia. It may be isolated from a number of sources including bacteria, plants and animal tissues, but not from humans. *Escherichia coli* produces two forms of this enzyme, designated type I and type II. The two types of L-asparaginases differ in a several aspects, some of which are detailed below:
 1. L-aparaginase I (L-PAR I) is an enzyme located in the cytoplasm, whereas L-PAR II is a secreted protein.
 2. The activity of L-PAR II is regulated by oxygen levels in the medium such that a high level of induction is obtained under anaerobic conditions.
 3. L-PAR II has a much higher affinity for is substrate than L-PAR I.
 4. The two enzymes have different solubility and chromatographic behavior as well as a different pH-dependent activity.

L-PAR II has been shown to inhibit the growth of a number of animal tumors in vivo, and to interfere with the synthesis of proteins in vitro. The anti-tumor activity of L-PAR II may result from the need of the cancer cells for their rapid, malignant growth and thus, survival a large amount of asparagines. These cancer cells use asparagines from the diet as well as from endogenously produced product (which is limited) to satisfy their large asparagines demand. Treatment of cancer cells with L-PAR II was found to cause increased hydrolysis of asparagine external to the cell, such that while normal cells are able to provide themselves with all the asparagine they need internally, cancer cells become depleted rapidly and die.

As will be shown in the following examples, it has now been found that healthy individuals and cancer patients show striking differences in their fecal microflora, and in particular in the levels of L-PAR II therein which let to the claimed invention. In particular, the present invention disclosed the correlation between levels of L-PAAR II and cancer cells, such that low levels of expression of L-PAR II or of activity of L-PAR II, indicate the presence of cancer cells in said subject and vice versa.

As will be appreciated by the skilled in the art, different bacteria may express L-PAR II. L-PAR II isolated from *E. coli* has been extensively studied and appears as a tetramer of approximately 140 kDa. Thus, according to one preferred embodiment of the invention, the bacteria identified and isolated for detection of the level of expression or activity of L-PAR II is *E. coli*.

The following description provides specific examples for executing the present invention. The present invention is defined by the claims, the contents of which are to be read as included within the disclosure of the specification, and will be described in the following non-limiting examples. It should be clear that other variations in form and detail of the invention may be possible without departing from the scope and spirit of the invention as herein disclosed.

EXAMPLE I

Materials

Mac Conkey agar; m-Endo Agar Les; Slanetz-Bartley agar; Bile-esculine-azide agar; Simmons citrate; MIO medium; Mueller Hinton agar; Esculine agar/TSA+6.5% NaCl (divided plate); and Indole test strips were all purchased from Hylabs, Park Tamar, Rehovot, Israel.

Methods

Preparation of fecal samples

Samples of feces were homogenized, weigh (5 gr. per sample) and introduced each into sterile, 50 ml, tubes. Each sample was then diluted with sterile Saline (20 ml), vortexed for approximately 10-15 seconds and then incubated upright at room temperature for approximately 15 minutes until large particles settle to the bottom of the tube. Alternatively, the samples may be spinned for 3 minutes at 400 rpm (Sorvall centrifuge) until the large particles settle at the bottom of the tube.

From each sample, the upper portion (i.e. not including the large particles) was removed and introduced into a second sterile tube further vortexing for approximately 5 seconds. Alternatively, a bacteriological loop may be dipped into the upper portion of the sample for removal of desired aliquots. The resulting samples were then optionally diluted with sterile Saline according to the following rations: $1:10^2$, $1:10^4$, $1:10^{10}$, $1:10^{12}$.

Preparation of microorganism colonies

Aliquots (100 µl) from the $1:10^2$ and $1:10^4$ diluted samples were homogeneously inoculated on dry Slanetz-Bartley and Bile-esculine-azide plates (for isolation of *Enterococcus sp*).

In addition, aliquots (100 µl cach) from the 1:1010 and 1:1012 dilutions were homogeneously inoculated on dry MacConkey (for isolation of coliform containing *Escherchia coli (E.coli)*). Mueller Hinton agar plates we used to determine Gram negative and total bacteria count and were inoculated in the same manner as with the MacConkey plates.

A sample from the untreated (undiluted) feces (10 µl) was spread on McConkey Agar plate or m-Endo Agar Les plates (the latter selective for coliform including *E. coli*. This "undiluted" sample is used to verify the "cleaning" and homogenization process does not change the final outcome in terms of types of bacteria and relative counting.

All plates were incubated for 12-24 hours at 37° C. until colonies of bacteria appeared on the plates. When necessary, typically with the Slanetz-Bartley and Bile-esculine-azide plates, incubation for up to 48 hours was performed.

All colonies grown on Mac-Conkey and Mueller Hinton plates were counted for determination of the total bacteria count.

*Enterococcus sp.* colonies appeared on the Slanetz-Bartley and Bile-esculine-azide plates as red or big black haloed colonies respectively. These *Enterococus sp.* colonies were counted. The percentage of the *Enterococci* colonies from the total number of colonies was determined.

Further, in m-endo-LES medium pink, off-white or blue-purple Coliform colonies appeared, being indicative for the presence of *E. coli* colonies.

*Streptococcus bovis* colonies were determined as those being Bile-Esculine positive and Group D antigen positive, however, NaCl (6.5%) negative and PYR negative.

For the formation of single colony plates, the following procedure was employed. By the use of a bacterialogical loop coliform colonies were picked (quantity depends on quantitative analysis of the sample in order to maintain the original ratio) from each plate and transferred onto a Mueller-Hinton Agar plat for incubation at 37° C.

Results

The presence or absence of *Enterococcus sp.* and/or *Streptococcus bovis* in the different plates was examined. *Enterococcus sp.* bacteria were identified as red colonies on Slanetz-Bartley or big black haloed colonies on Bile-esculine-azide as described above as well as those colonies that were Bile-Esculine positive and NaCl (6.5%) positive.

*Streptococcus bovis* colonies were determined as those being Bile-Esculine positive and Group D antigen positive (*enterococci* bear the Lancefield Group D antigen, however, NaCl (6.5%) negative and PYR negative (*Enterococcus* produces to a positive PYR test (red color produced after addition of N, N methyl aminocynnamaldehyde reagent after exposure to L-pyrrolidonyl-beta-naphtylamide (PYR) substrate). *Streptococcus bovis* was determined in the same manner.

The following Table 1 shows the results obtained. Positive results are indicated by "+" in the table.

TABLE 1

|  | Bile-Esculin | NaCl (6.5%) | PYR | Group D Antigen |
|---|---|---|---|---|
| Enterococcus sp | + | + | + | + |
| Streptococcus bovis | + | − | − | + |

As indicated above, MacConkey Agar plates supports growth of coliform containing *Enterobacteria* (*E.coil*). Typically, *E. coli* appears as red colonies (lactose positive). In order to determine the fraction of *E.Coli* from the total *Enterococci* colonies and thereby from the total bacteria count, the following tests were performed. (a) Indol test; (b) Simmons Citrate test; (c) Ornitine decarboxylase (ODC); and (d) motility test.

*E.coli* colonies were determined only when 98% of the bacteria were Indol positive; 99% of the bacteria were Simmons Citrate negative; 65% of the bacteria were Ornitine decarboxylase (ODC) positive; and 95% of the bacteria were motile.

Alternatively, the indol, ODC and motility tests may be performed using an MIO medium which enables conducting all three test in a single procedure.

The fraction of *E.coli* from the total coliform was determined by calculating the percentage of red colonies from the, total amount of colonies grown in the same Slanetz-Bartley agar plate or by calculating the percentage of red colonies on Slanetz-Bartley plates from the total amount of colonies on Mueller-Hinton plates (more accurate). The analysis was performed using a spectrophotometer.

EXAMPLE II

Incubation of bacteria with cancer cells

For evaluating the effect of the feces-derived microorganism on cancer cells, the following procedure was performed:

A suspension of cancer cells (concentration of 4×104 cells/100 μl), in serum-free DMEM was introduced into 96 well plates (6 duplicates for each stool sample).

Mueller-Hinton plates containing bacteria were washed with 10-ml DMEM and the bacterial suspension obtained was collected in 15-ml tubes. Aliquots of bacterial suspension (50 μl of bacterial suspension ($2\times10^6$ bacteria/ml)) were then introduced into the tumor cell-containing wells.

For the formation of single colony plates, the procedure as described above was employed. In particular, by the use of a bacteriological loop coliform colonies were picked (quantity depends on quantitative analysis of the sample in order to maintain the original ratio) from each plate and transferred onto a Mueller-Hinton Agar plat for incubation at 37° C. to form the diagnostic sample for further incubation with the cancer cells.

Cancer cells-containing wells, in which no bacteria were introduced, were used as a regular negative control.

All wells were then incubated for 4 hours at 37° C. after which the content of each well was mixed and aliquots of the well content (130 μl) were dried on glass slides at room temperature until the slides became dry followed by fixation of the cells on the slide and staining of the cells according to manufacturer instructions using the Giemsa stain kit (Merck).

The extent of interaction between the test sample of bacteria and the standard culture of cancer cells is made by counting the number of cancer cells remaining in the visual field of the microscope, after and dyeing as necessary. The operative methods for counting cells on a microscope slide are per se known to persons in the field and include, for example human manual counting or by the use of an Automated Computer Assisted Microscope (ACAM) using a pre-defined algorithm (by counting 64 fields per glass slide).

The automated Computer Assisted Microscope disclosed herein, performs the following principal steps:

1) A three dimensional (3D) Auto-Focus is directed at the depth of the cells and not to the bacteria. Cells only from the slide window;
2) By the use of a counting software, the cells are classified as high relevant, relevant, not relevant, highly not relevant cells, etc., by analyzing each cell object to determine if its external membrane has not been disrupted (by the bacteria) or is "damaged", i.e. at least partially lysed by the bacteria;
3) Further, by the use of the software, cells are differentiated from other objects of the same size and of a similar shapes (including Gimza dry stains);
4) Yet further, by the use of the counting software, cells are counted in a predefined window in order to minimize any deviations in the resulting index as defined below.

A Tumor Cell Necrosis Index (TCNI) may be calculated which is indicative of the number of surviving cancer cells. The TCNI may be determined according to the following equation:

$$(a-b)/a \times 100 = C$$

wherein

C=the tumor cell necrosis index (TCNI)

a=the number of cancer cells in the negative control samples (without the bacteria) or the number of standard cancer cells destroyed in the presence of the 'control' bacteria;

b=the number of cancer cells not destroyed by the tested sample.

Qualitatively, it will be apparent that in a healthy patient in which the intestinal bacteria have a similar activity to the 'control' sample, b will be low giving a relatively high TCNI, whereas with cancer patients carrying cancerolytic cells b will have a relatively high value and the TCNI will be lower.

Results

FIGS. 2A and 2B show microscope pictures of the result of incubation of bacteria samples obtained from cancer patients or healthy subjects (diagnostic samples as prepared by the method of the present invention) with the standard cancer cells. In particular, a larger amount of viable cancer cells are visualized in the culture treated with a sample obtained from sick subject (FIG.2A), as compared to the result obtained with a bacteria sample obtained from healthy subject (FIG.2B).

The results obtained were analyzed statistically based on a group containing 110 subject, of which 38 were active cancer patients, 36 were cancer patients with no evidence of disease (i.e. potentially cured, also referred to as cancer NED subjects) and 36 were healthy subjects.

In the following analysis three cut-off values of TCNI were determined 50% cut-off, 60% cut off and 70% cut-off. For example, in the case of 60% cut-off, if upon mixing the bacteria with cancer cells more than 60% of the cells were destroyed then the test was regarded as negative for cancer while if 60% or less of the cells were destroyed, the test was considered positive for cancer.

The following statistical results, were obtained (95% confidence limits):

|  | 70% cut-off Sensitivity | 60% cut-off Sensitivity | 50% cut-off Sensitivity |
|---|---|---|---|
| Active cancer | 74% | 68% | 61% |
| Non-cancer | 61% | 81% | 86% |
| Non-cancer | Specificity 61% | Specificity 81% | Specificity 86% |

These results which had been obtain from General population without selection show that the screening method of the present invention is sufficiently sensitive, i.e. capable of testing cancer patients as positive for cancer as well as highly specific, i.e. capable of testing healthy subjects as negative for cancer).

In addition, for a chosen cut-off of 60% the Wilcoxon Rank Sum Test was used in order to determine whether there is a statistically significant shift in the index values between the cancer groups and the non cancer groups. A rank-sum normal statistic with correction Z=−4.25, and p-value <0.0001 was obtained. This result shows that there is a statistically significant difference between the distribution of test scores in active cancer group and non cancer groups.

The effect of antibiotics on the validity on the index values was also evaluated. Out of the tested subjects, 1 of the 38 active subjects and 10 of the non-cancer subject were treated with antibiotics. In the former case an index value of 24 was obtained as compared to a mean value of 44.2 for the remainder of the group members, while in the latter case a mean index value of 74.5 was obtained as compared to 66.9 among the remainder of the group members.

These results may suggest that there is no apparent effect of treatment with antibiotics on the TCNI obtained.

EXAMPLE III

Characterization of fecal bacteria derived L-PAR

In order to characterize L-PAR from fecal bacteria, the expression levels of the enzyme by fecal derived bacteria was determined. Assessment of the level of expression was performed by Immunoblots, using a specific antibody, and by assessing the amount of specific mRNA using conventional molecular methods such as reverse transcription (RT)-PCR. In addition, L-PAR II activity may be directly evaluated by the use of a standard enzymatic assay.

Immunoblot

Fecal bacteria were grown anaerobically, collected and disrupted by sonication. Bacteria proteins were separated by polyacrylamide gel electrophoresis, blotted to nitrocellulose and probed with asparaginase II-specific antisera.

RT-PCR

Reverse transcription (RT)-PCR is a valuable tool widely used for gene expression. In bacteria, RT-PCR is helpful beyond standard protocols of northern blot RNA/DNA hybridization to identify specific transcripts. RT-PCR has been successfully used with different microorganisms such as *S. aureus, C. botulinum, M. tuberculosis* and fungi.

Accordingly, in order to assess the transcription level of the enzyme bacteria is grown anaerobically from which bacterial RNA is isolated quantitative RT-PCR is performed using primers specific to L-PAR II (according to published gene sequence of this enzyme). The sequence of the L-ASPARAGINASE II is well defined and may be available, inter alia, through NCBI (Accession No. M34277).

It has been found that the presence of L-PAR II mRNA could be detected without the need of amplification of the sequence by RT-PCR, while, in order to detect the mRNA from samples obtained from cancer patients one or more RT-PCR amplifications were required. These results teach the correlation between the level of expression of L-PAR II and the probability of a subject to have cancer, i.e. feces derived bacteria from healthy subjects have a high level of expression of L-PAR II while feces-derived bacteria from sick subject have a lower level of expression of L-PAR II.

L-Asparaginase Enzymatic Assay

Spheroplasts are generated by treating anaerobically grown bacteria with lysozyme and EDTA following osmotic shock. Under these conditions, L-PAR II has been shown to be released into the medium while most of the L-PAR I remain intracellularly.

Asparaginase activity is assayed using the method of direct Nesslerization of ammonia according to which the rate of hydrolysis of asparagine by the enzyme is determined. In particular, ammonia reacts with Nessler's reagent to form a yellowish-brownish complex that can be quantified by spectrophotometer. Nessler reagent is an alkaline solution of potassium mercuric iodide commonly used in analytical chemistry, especially for testing the presence of ammonia in aqueous solutions (water sample blood sample or urine, sample).

Alternatively, it is possible to determine L-PAR II levels in mixtures of the two isoforms (I and II). The method requires calculation of the ratio of activity at pII 5.0 and pH 8.4 and applying a mathematical equation to correct the contribution of the activity of each isoform.

The invention claimed is:

1. A method for diagnosis of malignant neoplasms derived from epithelial tissue cells in a subject comprising the steps of:
   (i) providing at least a first and second fecal sample from said subject;
   (ii) treating said fecal samples to obtain feces-derived bacteria samples;
   (iii) identifying in the feces-derived bacteria samples one or more types of bacteria;
   (iv) determining for each of said one or more types of bacteria its relative fraction from a total count of bacteria in one of the feces-derived bacteria samples;
   (v) isolating one or more types of bacteria from one or both of the feces-derived bacteria samples;
   (vi) preparing a diagnostic sample containing bacteria of the one or more types isolated in step (v), the fraction of each of the one or more types of bacteria in said diagnostic sample corresponding to the relative fraction thereof in the fecal samples, as determined in step (iv);
   (vii) interacting said diagnostic sample with cells for a time period sufficient to detect lysis of said cells, thereby determining for said fecal sample a tumor cell necrosis index (TCNI) with the following equation:

$(a-b)/a \times 100 = C$ wherein
   C=the tumor cell necrosis index (TCNI)
   a=the number of cells in the negative control samples (without the bacteria) or the number of standard cells destroyed in the presence of the control bacteria;
   b=the number of cells not destroyed by the tested sample; and
   (viii) diagnosing said subject as having or not having a malignant neoplasms derived from epithelial tissue cells in accordance with the TCNI value determined in step (vii).

2. A method for diagnosis of malignant neoplasms derived from epithelial tissue cells in a subject comprising the steps of:
   (i) providing at least a first and second fecal sample from said subject;
   (ii) treating said fecal samples to obtain feces-derived bacteria samples;
   (iii) identifying in the feces-derived bacteria samples more than one type of bacteria;
   (iv) determining for each of said more than one type of bacteria its relative fraction from a total count of bacteria in one of the feces-derived bacteria samples;
   (v) isolating one or more types of bacteria from said one of the feces-derived bacteria samples;
   (vi) preparing a diagnostic sample containing the bacteria isolated in step (v), the fraction of each of the more than one type of bacteria in said diagnostic sample corresponding to the relative fraction thereof as determined in step (iv);
   (vii) interacting said diagnostic sample with cells for a time period sufficient to detect lysis of said cells, thereby determining for said fecal sample a tumor cell necrosis index (TCNI)) with the following equation:

$(a-b)/a \times 100 = C$ wherein
   C=the tumor cell necrosis index (TCNI)
   a=the number of cells in the negative control samples (without the bacteria) or the number of standard cells destroyed in the presence of the control bacteria;
   b=the number of cells not destroyed by the tested sample; and
   (viii) diagnosing said subject as having or not having a malignant neoplasms derived from epithelial tissue cells in accordance with the TCNI value determined in step (vii).

3. The method of claim 1, wherein said feces-derived bacteria are selected from the group consisting of *Escherichia coli, Streptococcus Bois,* and *Enterococcus* or a mixture thereof.

4. The method of claim 1, wherein said fecal sample is a human fecal sample.

5. The method of claim 4, wherein contamination is removed from said fecal sample to obtain an uncontaminated feces-derived bacteria sample.

6. The method of claim 1, wherein said bacteria are isolated from colonies formed on selective culture mediums.

7. The method of claim 1, wherein said relative fraction of each said bacteria types of step (iv) is determined by calculating the percentage of each said bacteria type from the total count of bacteria in the same bacteria sample.

8. The method of claim 1, wherein said bacteria are Gram-negative anaerobic bacteria.

9. The method of claim 8, wherein said Gram-negative anaerobic bacteria is of a genus selected from the group consisting of *Escherichia, Salmonella, Shigella, Klebsiella, Yersinia, Enterobacter, Haemophilus, Gardnerella* and *Pasteurella*.

10. The method of claim 9, wherein the bacteria is *E. coli*.

11. The method of claim 10, wherein the *E. coli* is isolated from the feces-derived bacteria by culturing the feces-derived sample of bacteria on a culture medium selective for *E. coli*.

12. The method of claim 11, wherein the culture medium is selected from the group consisting of MacConkey agar and m-Endo agar.

13. The method of claim 7, wherein said bacteria are Gram-positive bacteria.

14. The method of claim 13, wherein said Gram-positive bacteria is of a genus selected from the group consisting of *Staphylococcus, Enterococcus, Streptococcus,* and *Lactococcus*.

15. The method of claim 14, wherein said bacteria is *Streptococcus bois* or *Enterococcus*.

16. The method of claim 15, wherein *Enterococi coliform* is isolated from said feces-derived bacteria sample by culturing the feces-derived sample of bacteria on a culture medium selective for *Enterococcus*.

17. The method of claim 16, wherein said culture medium is selected from the group consisting of the Slanetz-Bartley agar and Bile-esculine-azid agar.

18. The method of claim 1, wherein said diagnostic sample is interacted with the cancer cells for a time period sufficient to determine the extent of interaction between the bacteria and the cancer cells.

19. The method of claim 18, wherein at the end of the time period, the number of interacted, non-interacted cancer cells or both present at the end of said time period is determined.

* * * * *